(12) United States Patent
Javadi

(10) Patent No.: US 7,821,631 B1
(45) Date of Patent: Oct. 26, 2010

(54) ARCHITECTURE OF LASER SOURCES IN A FLOW CYTOMETER

(76) Inventor: Shervin Javadi, 17441 El Rancho Ave., Monte Sereno, CA (US) 95030

( * ) Notice: Subject to any disclaimer, the term of this patent is extended or adjusted under 35 U.S.C. 154(b) by 287 days.

(21) Appl. No.: 12/148,016

(22) Filed: Apr. 16, 2008

Related U.S. Application Data

(60) Provisional application No. 60/925,460, filed on Apr. 20, 2007.

(51) Int. Cl.
*G01N 21/01* (2006.01)
(52) U.S. Cl. .................................................... 356/244
(58) Field of Classification Search .......... 356/244–246
See application file for complete search history.

(56) References Cited

U.S. PATENT DOCUMENTS

| | | | | |
|---|---|---|---|---|
| 3,941,487 A | * | 3/1976 | Ehret et al. ................. | 356/411 |
| 4,818,103 A | * | 4/1989 | Thomas et al. ................. | 356/72 |
| 2005/0249642 A1 | * | 11/2005 | Okun et al. .................. | 422/103 |
| 2007/0189925 A1 | * | 8/2007 | Blecka et al. .................. | 422/64 |
| 2007/0237679 A1 | * | 10/2007 | Hegazi ..................... | 422/82.08 |
| 2008/0291425 A1 | * | 11/2008 | Norton et al. .................. | 356/39 |

* cited by examiner

*Primary Examiner*—Michael P Stafira

(57) ABSTRACT

The architecture of air-coupled laser sources in a flow cytometer is provided. The flow cytometer includes a mounting plate with a first major surface and a second major surface. A cuvette is mounted on the first major surface and a fluid core stream flows through the cuvette essentially parallel to the major surfaces of the mounting plate. A first air-coupled laser source is mounted on the first major surface. The first air-coupled laser source generates a first laser beam. The flow cytometer also includes a first beam-shaping optic system corresponding to the first air-coupled laser source. The first beam-shaping optic system receives the first laser beam and focuses it at the center of the fluid core stream perpendicular to the fluid core stream.

10 Claims, 4 Drawing Sheets

ARCHITECTURE OF LASER SOURCES IN A FLOW CYTOMETER

CROSS REFERENCE TO RELATED APPLICATIONS

This application claims the benefit of Provisional Application No. 60/925,460, filed Apr. 20, 2007, which is incorporated by reference herein.

FIELD OF INVENTION

The invention disclosed here relates in general to the field of flow cytometers, and more particularly, to the architecture of laser sources in a flow cytometer.

BACKGROUND

Flow cytometers are laboratory instruments that are used for identifying the particles present in a fluid and the properties of the particles. Cytometers use the principle of light scattering and fluorescence to generate data pertaining to the particles present in the fluid. The fluid is in some cases hydrodynamically focused so that the particles line up single file in a relatively small fluid core stream. Thereafter, a laser beam is passed through this fluid core stream. After the laser beam strikes the particles in the fluid core stream, these particles emit fluorescence and reflect or scatter the incident light. The emission, the scattered light, and the reflected light are directed to detectors by using lenses, mirrors or other optical elements.

Some commercially available cytometers use laser sources which are air-coupled to the fluid core stream, i.e., the laser light is not directed to the fluid core stream using fiber optic cables. These cytometers attach one or more laser sources to a mounting plate, which is perpendicular to the fluid core stream. The lasers may be attached to the mounting plate either directly or with the aid of mounting brackets. The fluid core stream passes through a cuvette where a laser beam, emitted by the laser source, is intercepted by the particles in the fluid core stream. The particles reflect, scatter or emit light when the laser beam strikes them.

Most commercial laser sources produce beams with a Gaussian profile. Consequently, the laser source has to be aligned to the fluid core stream to ensure that the particles in the fluid core stream intercept the beam at the center, where the beam is at its highest intensity. Since a Gaussian beam exerts the maximum intensity at its center, cytometers with a Gaussian beam source need to exert precise control over flow, location and diameter of the fluid core stream to ensure that the beam strikes the particles with the maximum intensity. To solve this problem, an elliptical laser beam is used in most cytometers. In an elliptical beam, the change in the beam intensity is less as one moves off center compared to a circular beam. Although elliptical beams have a smaller decrease in beam intensity across their center, the total intensity of the beam at its center is reduced compared to a circular beam.

In cases where the laser light is air coupled, temperature changes within the device affect the laser alignment, based on the method used to mount the cuvette and materials used in the whole assembly. As a result, the alignment of the laser source with the fluid core stream can get altered due to the differential thermal expansion of the components used to mount the laser source and cuvette. Consequently, erroneous results can be generated by the cytometer.

Some of the existing commercially available cytometers use fiber optic cables to reduce the effect of differential thermal expansion. In these cytometers, fiber optic cables are used to deliver the laser beam from the source to the cuvette. The fiber optic cables may be mounted on mounting plates which are parallel or perpendicular to the core stream. This can reduce the thermally induced misalignment. However, this decreases the laser light delivered to the sample due to greater losses in the fiber optic cables.

In light of the foregoing details, there is a need for a laser-architecture for cytometers that can reduce the effect of differential thermal expansion on the alignment of the air-coupled laser sources to the fluid core stream. The architecture should use air-coupled lasers to eliminate the losses caused by the use of fiber optic cables.

BRIEF DESCRIPTION OF THE DRAWINGS

The preferred embodiments of the invention will hereinafter be described in conjunction with the appended drawings, provided to illustrate and not to limit the invention, wherein like designations denote like elements, and in which.

DETAILED DESCRIPTION OF THE INVENTION

Figure 1:
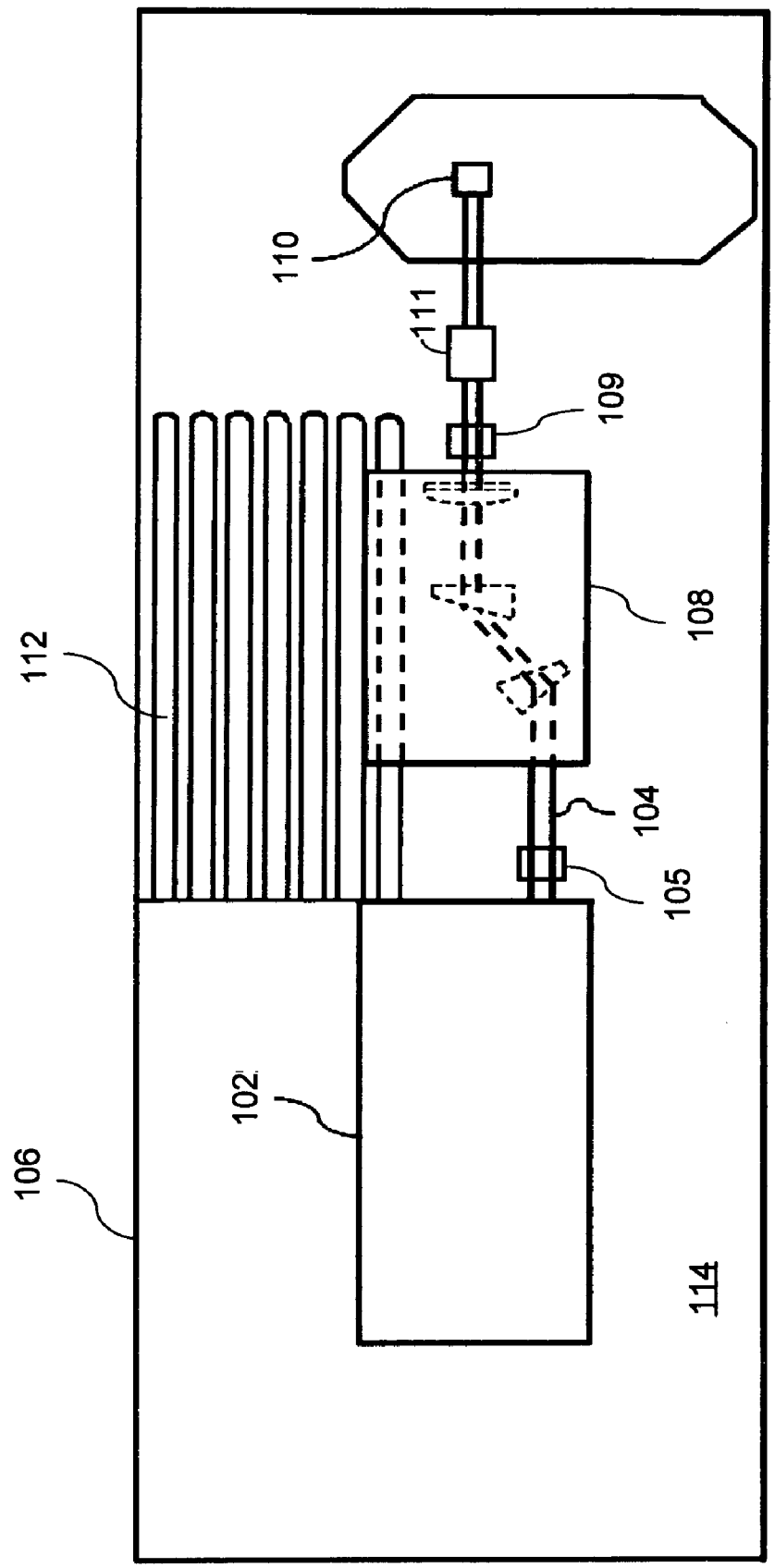
FIG. 1 illustrates a front view of a flow cytometer in accordance with an embodiment of the present invention.

While the preferred embodiments of the invention have been illustrated and described, it will be clear that the invention is not limited to these embodiments only. Numerous modifications, changes, variations, substitutions and equivalents will be apparent to those skilled in the art, without departing from the spirit and scope of the invention.

An object of the present invention is to provide a flow cytometer comprising a laser architecture that can reduce the effect of differential thermal expansion on the alignment of the air-coupled laser sources to the fluid core stream, and reduce cost, complexity and number of parts used in the flow cytometer.

Another object of the present invention is to provide a flow cytometer comprising air-coupled laser sources that can eliminate the losses caused by the use of fiber optic cables.

To achieve the objectives of the present invention, in an embodiment of the present invention, a flow cytometer is provided. The flow cytometer includes a mounting plate with a first major surface and a second major surface. Further, the flow cytometer includes a cuvette mounted to the first major surface. A fluid core stream flows through the cuvette essentially parallel to the major surfaces of the mounting plate. Further, the flow cytometer includes at least one air-coupled laser source mounted on at least one of the first major surface and the second major surface. The at least one air-coupled laser source generates a corresponding laser beam. Furthermore, the flow cytometer includes at least one beam-shaping optic system corresponding to the at least one air-coupled laser source. The at least one beam-shaping optic system receives the corresponding laser beam from the at least one air-coupled laser source and focuses it at the center of the fluid core stream.

In another embodiment of the present invention, a flow cytometer is provided which includes a mounting plate with a first major surface and a second major surface. Further, the flow cytometer includes a cuvette mounted on the first major surface. A fluid core stream flows through the cuvette essentially parallel to the major surfaces of the mounting plate. Further, the flow cytometer includes at least one air-coupled laser source mounted on at least one of the first major surface and the second major surface. The at least one air-coupled laser source generates a corresponding laser beam. Further, the flow cytometer includes a plurality of fins provided on the mounting plate. The plurality of fins cool the at least one air-coupled laser source. Further, the flow cytometer includes a plurality of spacers mounted on the mounting plate. The plurality of spacers are located between the at least one air-coupled laser source and the mounting plate. Further, the plurality of spacers can also be placed between the cuvette and the mounting plate. Furthermore, the flow cytometer includes at least one beam-shaping optic system corresponding to the at least one air-coupled laser source. The at least one beam-shaping optic system receives the corresponding laser beam from the at least one air-coupled laser source and focuses it at the center of the fluid core stream.

In yet another embodiment of the present invention a flow cytometer is provided which includes a mounting plate with a first major surface and a second major surface. Further, the flow cytometer includes a cuvette mounted on the first major surface. A fluid core stream flows through the cuvette parallel to the major surfaces of the mounting plate. Further, the flow cytometer includes a first air-coupled laser source mounted on the first major surface. The first air-coupled laser source generates a first laser beam. Furthermore, the flow cytometer includes a first beam-shaping optic system corresponding to the first air-coupled laser source. The first beam-shaping optic system receives the first laser beam from the first air-coupled laser source and focuses it at the center of the fluid core stream which facilitates an analysis of the fluid core stream. Further, the flow cytometer includes a second air-coupled laser source mounted on the second major surface. The second air-coupled laser source generates a second laser beam. Furthermore, the flow cytometer includes a second beam-shaping optic system corresponding to the second air-coupled laser source. The second beam-shaping optic system receives the second laser beam from the second air-coupled laser source and focuses it at the center of the fluid core stream which facilitates an analysis of the fluid core stream.

FIG. 1 illustrates a front view of a flow cytometer 100 in accordance with an embodiment of the present invention. The flow cytometer 100 includes a mounting plate 106 with a first major surface 114 and a second major surface 116 (shown in FIG. 2). The flow cytometer 100 also includes a cuvette 110, at least one air-coupled laser source generating a corresponding laser beam, at least one laser beam steering plate and at least one beam-shaping optic system corresponding to the at least one air-coupled laser source. For the purpose of this description, the flow cytometer 100 is shown to include a first air-coupled laser source 102 that produces a first laser beam 104, the mounting plate 106, a first laser beam steering plate 105, a first beam-shaping optic system 108, a second laser beam steering plate 109, the cuvette 110 and a waveplate 111. Examples of the first air-coupled laser source 102 include, but are not limited to, a diode laser, a gas laser, and/or any other commercially available laser, which can be selected depending on the size and wavelength required to analyze a fluid. The first air-coupled laser source 102 is mounted on the first major surface 114 of the mounting plate 106. The cuvette 110 that holds a fluid core stream to be analyzed is also mounted on the first major surface 114, either directly or indirectly. In the case of indirect mounting, the cuvette 110 can be fitted in an incubator or flow cell, which can then be mounted on the first major surface 114. The cuvette 110 receives a steady flow of fluid from a container holding the fluid.

Further, the fluid core stream flows essentially parallel to the major surface 114 of the mounting plate 106. Further, a mechanism is usually provided with the flow cytometer 100 to ensure a laminar fluid core stream. However, since this invention deals with the architecture of air-coupled laser sources in the flow cytometer 100, this mechanism has not been shown in FIG. 1.

Further, in an embodiment, the flow cytometer 100 can also include a plurality of fins. For the purpose of this description, the flow cytometer 100 is shown to include a plurality of fins 112. In an embodiment, the plurality of fins 112 can be an integral part of the mounting plate 106. In another embodiment, the plurality of fins 112 can be attached to the mounting plate 106. Further, the first beam-shaping optic system 108 can include one or more lenses, prisms or other optical elements.

The first air-coupled laser source 102 produces the first laser beam 104 that passes through the first laser beam steering plate 105. The first laser beam steering plate 105 can be used to shift the path of the first laser beam 104. For example, rotating the first laser beam steering plate 105 about an axis that is mutually perpendicular to the first laser beam 104 and the major surfaces 114 and 116 of the mounting plate 106 the first laser beam 104 can be shifted in a vertical direction essentially parallel to the major surfaces 114 and 116 of the mounting plate 106. Similarly, rotating the first laser beam steering plate 105 about an axis that is perpendicular to the first laser beam 104 and parallel to the major surfaces 114 and 116 of the mounting plate 106 the first laser beam 104 can be shifted in a horizontal direction essentially perpendicular to the major surfaces 114 and 116 of the mounting plate 106. Further, the shift in the first laser beam 104 by rotating the first laser beam steering plate 105 can be used to align the first laser beam 104 with the center of the fluid core stream.

Further, the first air-coupled laser source 102 produces a first laser beam 104 that has a Gaussian profile. To obtain a beam with maximum intensity over a broader portion of its profile i.e. to make the beam non-circular, the first laser beam 104 is passed through the first beam-shaping optic system 108. The first laser beam 104 exiting the first beam-shaping optic system 108 is aligned with the center of the fluid core stream using the second laser beam steering plate 109. The second laser beam steering plate 109 functions in a manner similar to first laser beam steering plate 105. Consequently, the first laser beam 104 strikes the particles present in the fluid core stream. Thereafter, the particles either emit fluorescence, or reflect or scatter the incident laser beam. Detectors, placed strategically in and around the flow cytometer 100 (not shown in the FIG. 1), detect the scattered, emitted or reflected light. The signals generated by the detectors are analyzed to find the properties of the particles present in the fluid core stream. For example, a sample of blood containing blood cells can be tested by using the flow cytometer 100. In this event, the detection of light scattered in the direction of the first laser beam 104 provides a user with information about the size and shape of the different types of blood cells present in the sample of blood.

The first air-coupled laser source 102 is mounted on the first major surface 114 of the mounting plate 106. Further, the first air-coupled laser source 102 is mounted in a plane that is essentially parallel to the fluid core stream. In an embodiment, the first air-coupled laser source 102 can be such that it produces the first laser beam 104 with a vertical polarization with respect to mounting plate 106, i.e. the plane of polarization of the first laser beam 104 is essentially perpendicular to the major surfaces 114 and 116 of the mounting plate 106. In this embodiment, the waveplate 111 is placed in between the first beam-shaping optic system 108 and the cuvette 110, to rotate the polarization of the first laser beam 104 produced by the first air-coupled laser source 102 by an angle of 90°. The waveplate 111 can be a quarter retardation waveplate or any other commercially available polarization rotator, which rotates the polarization angle of the incident first laser beam 104 by 90° if necessary. Furthermore, the waveplate 111 can be placed in a number of different locations based on the specific optics used in the first beam-shaping optic system 108. If the first laser beam 104 emitted by the first air-coupled laser source 102 has a horizontal polarization with respect to the mounting plate 106, i.e. the plane of polarization of the first laser beam 104 is essentially parallel to the major surfaces 114 and 116 of the mounting plate 106, the waveplate 111 can be removed. Further, in an embodiment, the mounting plate 106 is provided with the plurality of fins 112 to cool the first air-coupled laser source 102 in the event of overheating.

Figure 2:
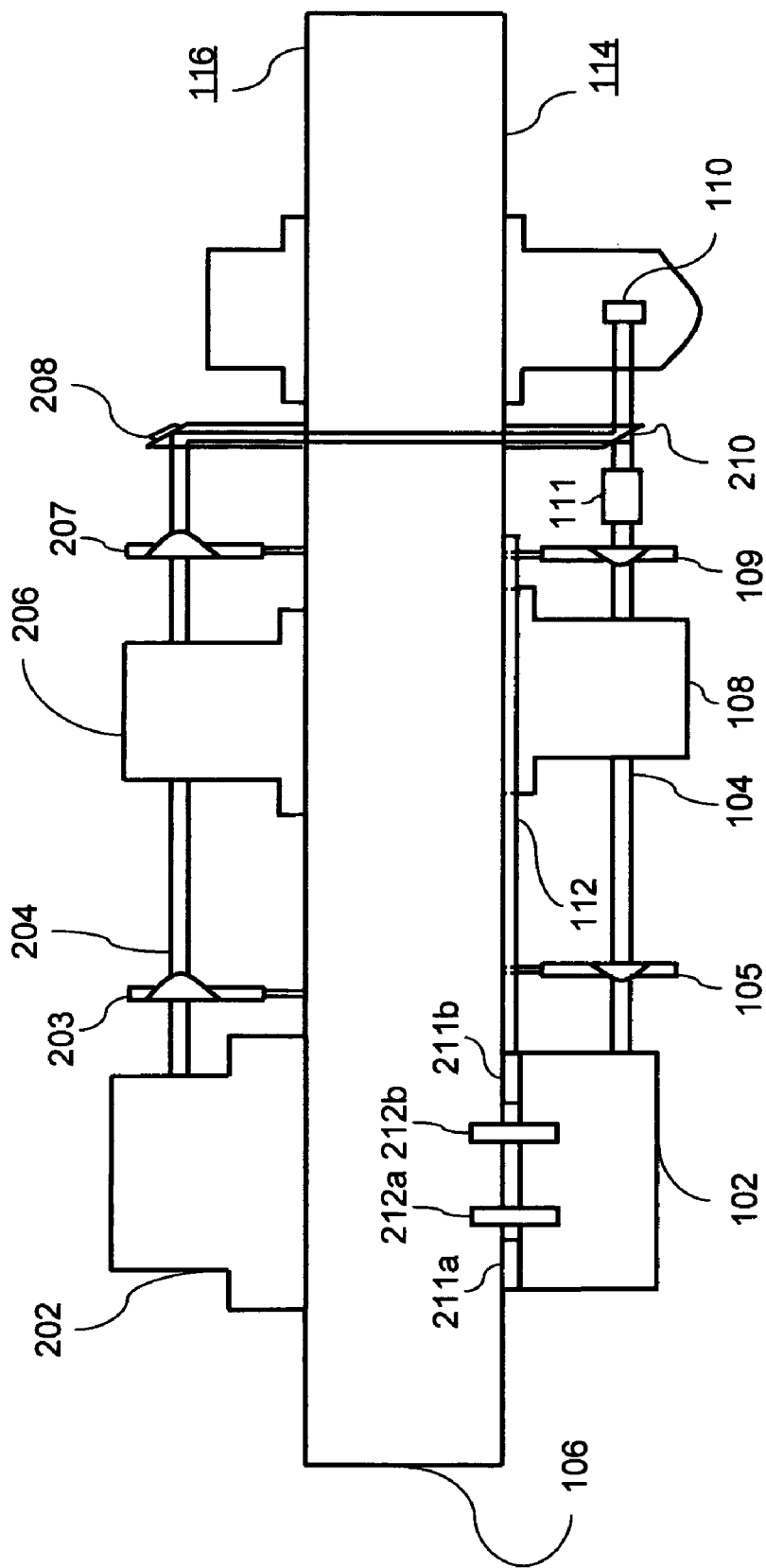
FIG. 2 illustrates a top view of the flow cytometer in accordance with an embodiment of the present invention.

In another embodiment, a plurality of spacers, for example the plurality of spacers 211a and 211b as shown in FIG. 2, can be used between the laser source 102 and the mounting plate 106. Further, in another embodiment the plurality of spacers 211a and 211b can also be used between the cuvette 110 and the mounting plate 106. Although, FIG. 2 is shown to include two spacers, it will be readily apparent to those with ordinary skill in the art that fewer or greater number of spacers can also be used to implement the present invention. Suitable materials can be chosen for the plurality of spacers 211a and 211b to compensate for the different coefficients of thermal expansion of the cuvette 110 and the first air-coupled laser source 102. Using the plurality of spacers 211a and 211b reduces differential thermal expansion in the flow cytometer 100, and thereby reduces the probability of misalignment between the first air-coupled laser source 102 and the cuvette 110.

FIG. 2 illustrates a top view of the flow cytometer 100 in accordance with an embodiment of the present invention. The flow cytometer 100 illustrated in FIG. 2 includes the same or similar elements to those described above with respect to FIG. 1. In addition to the first air-coupled laser source 102, the mounting plate 106, the first laser beam steering plate 105, the first beam-shaping optic system 108, the second laser beam steering plate 109, the cuvette 110, the waveplate 111, the plurality of fins 112 and the plurality of spacers 211a and 211b, the flow cytometer 100 is also shown to include a second air-coupled laser source 202, a second laser beam 204 emitted by the second air-coupled laser source 202, a third laser beam steering plate 203, a second beam-shaping optic system 206 corresponding to the second air-coupled laser source 202, a fourth laser beam steering plate 207, a first mirror 208, and a first dichroic mirror 210.

As shown in the FIG. 2, with the first air-coupled laser source 102 being mounted on the first major surface 114 of the mounting plate 106, the second air-coupled laser source 202 is mounted on the second major surface 116 of the mounting plate 106. In an embodiment, a plurality of mounting brackets, for example a plurality of mounting brackets 212a and 212b, can be used to mount the first air-coupled laser source 102 on the first major surface 114 of the mounting plate 106. Further, in an embodiment, the second air-coupled laser source 202 can also be mounted with the aid of mounting brackets similar to the plurality of mounting brackets 212a and 212b. The second air-coupled laser source 202 is selected in such a way that the flow cytometer 100 can be used to analyze the fluid core stream with laser beams of different wavelengths. The second air-coupled laser source 202 produces the second laser beam 204 that passes through the third laser beam steering plate 203. The third laser beam steering plate 203 can be used to shift the path of the second laser beam 204. For example, rotating the third laser beam steering plate 203 about an axis that is mutually perpendicular to the second laser beam 204 and the major surfaces 114 and 116 of the mounting plate 106 the second laser beam 204 can be shift in a vertical direction essentially parallel to the major surfaces 114 and 116 of the mounting plate 106. Similarly, rotating the third laser beam steering plate 203 about an axis that is perpendicular to the second laser beam 204 and parallel to the major surfaces 114 and 116 of the mounting plate 106 the second laser beam 204 can be shift in a horizontal direction essentially perpendicular to the major surfaces 114 and 116 of the mounting plate 106. Further, the shift in the second laser beam 204 by rotating the third laser beam steering plate 203 can be used to align the second laser beam 204 with the center of the fluid core stream.

Further, the second laser beam 204 is passed through the second beam-shaping optic system 206 that makes it non-circular and of maximum intensity over a broader portion of its profile. The second beam-shaping optic system 206 can include elements that are the same or similar to the elements of the first beam-shaping optic system 108. In an embodiment of the present invention, the first air-coupled laser source 102 and the second air-coupled laser source 202 can use a common beam-shaping optic system.

The second laser beam 204 exiting the second beam-shaping optic system 206 is aligned with the center of the fluid core stream using the fourth laser beam steering plate 207. The fourth laser beam steering plate 207 functions in a manner similar to the third laser beam steering plate 203. The second laser beam 204, after having passed through the fourth laser beam steering plate 207, is reflected by the first mirror 208. The first mirror 208 is so placed as to reflect the second laser beam 204 towards the first dichroic mirror 210. The first dichroic mirror 210 is capable of reflecting the laser beams of a particular wavelength and transmitting the beams of other wavelengths. The first dichroic mirror 210 can be selected is such a way that it transmits the first laser beam 104 and reflects the second laser beam 204. The first dichroic mirror 210 can be a high-pass or a low-pass filter, depending on the type of laser beam the first air-coupled laser source 102 produces.

Once the second laser beam 204 is directed towards the fluid core stream held in the cuvette 110, the fluid core stream emits fluorescence, or scatters or reflects the incident light. The emitted, scattered or reflected light is detected by detectors placed in and around the flow cytometer 100. The signals produced by the detectors are analyzed to find the properties of the particles present in the fluid core stream.

The second air-coupled laser source 202 is mounted on the second major surface 116 of the mounting plate 106. Further, the second air-coupled laser source 202 is mounted in a plane that is essentially parallel to the fluid core stream. In an embodiment, the second air-coupled laser source 202 can be such that it produces the second laser beam 204 with a vertical polarization with respect to mounting plate 106, i.e. the plane of polarization of the second laser beam 204 is essentially perpendicular to the major surfaces 114 and 116 of the mounting plate 106. In this embodiment, a waveplate similar to the waveplate 111 can be placed in between the second beam-shaping optic system 206 and the cuvette 110, to rotate the second laser beam 204 produced by the second air-coupled laser source 202 by a polarization angle of 90°. If the second laser beam 204 emitted by the second air-coupled laser source 202 has a horizontal polarization with respect to the mounting plate 106, i.e. the plane of polarization of the second laser beam 204 is essentially parallel to the major surfaces 114 and 116 of the mounting plate 106, the waveplate similar to the waveplate 111 can be removed.

Figure 3:
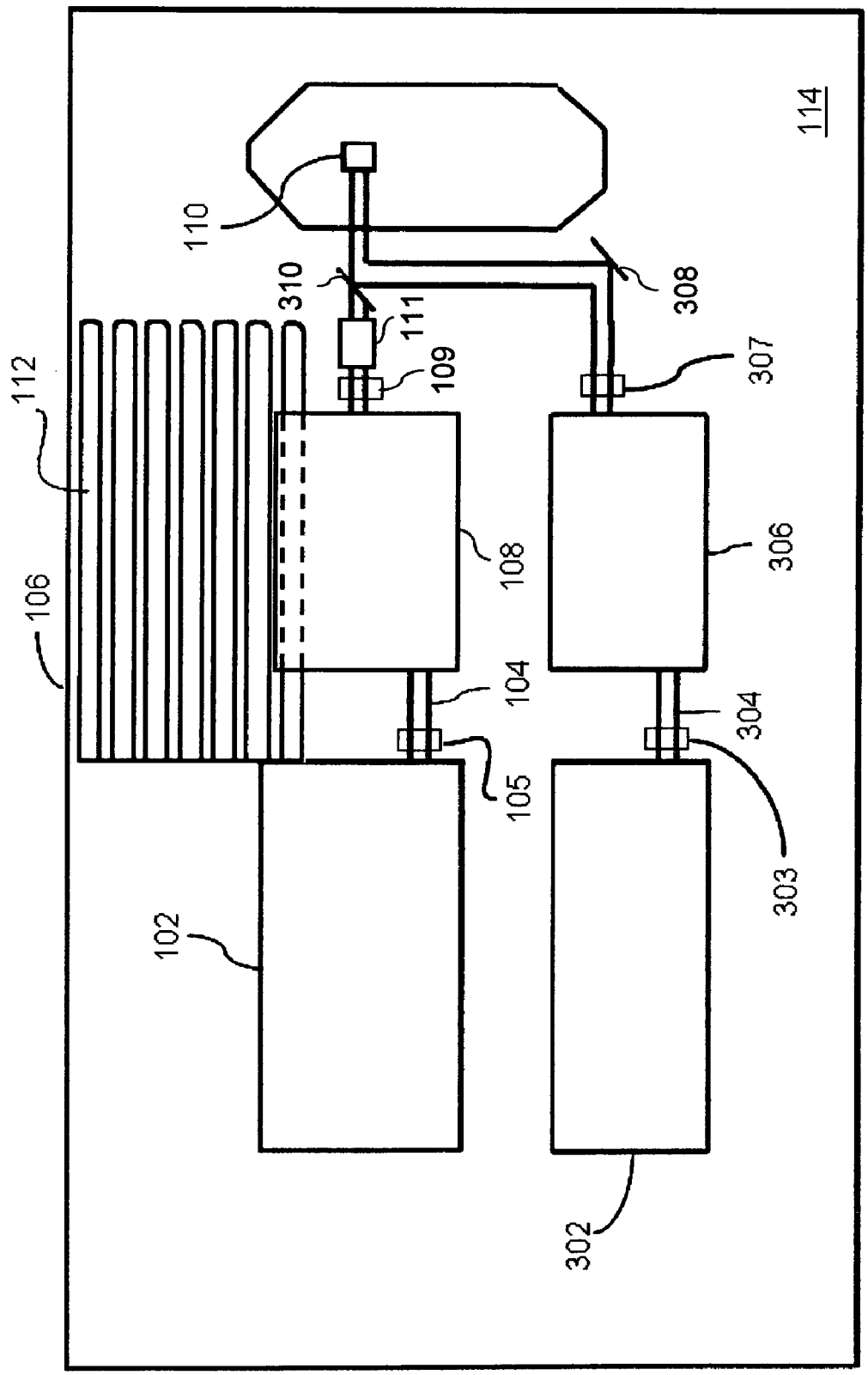
FIG. 3 illustrates a front view of the flow cytometer in accordance with another embodiment of the present invention.

FIG. 3 illustrates a front view of the flow cytometer 100, in accordance with another embodiment of the present invention. The flow cytometer 100 of FIG. 3 includes the same or similar elements to those described above with respect to FIG. 1. In addition to the elements, the first air-coupled laser source 102, the mounting plate 106, the first beam-shaping optic system 108, the cuvette 110 and the plurality of fins 112, the flow cytometer 100 shown in FIG. 3 can include a third air-coupled laser source 302 that emits a third laser beam 304, a fifth laser beam steering plate 303, a third beam-shaping optic system 306, a sixth laser beam steering plate 307, a second mirror 308, and a second dichroic mirror 310.

The third air-coupled laser source 302 is mounted on the mounting plate 106 below the first air-coupled laser source 102. In an embodiment, the third air-coupled laser source 302 can also be mounted with the aid of mounting brackets similar to the plurality of mounting brackets 212a and 212b, as shown in FIG. 2.

Further, the third air-coupled laser source 302 is selected in such a way that it provides the flow cytometer 100 with an increased number of wavelengths required to perform a more detailed analysis of the fluid. The third laser beam 304 is focused towards the center of the fluid core stream and is made non-circular with the help of the third beam-shaping optic system 306. In another embodiment, the flow cytometer 100 can have the first, the second and the third air-coupled laser sources. In one arrangement of this embodiment all the three air-coupled laser sources can use the same beam-shaping optic system to increase the intensity and width of the laser beams they emit. The second mirror 308 and the second dichroic mirror 310 can be used to combine the third laser beam 304 with the first laser beam 104.

The third air-coupled laser source 302 is aligned in a plane that is parallel to the major surfaces 114 and 116 of the mounting plate 106. This alignment is performed in such a way that the third laser beam 304 is directed towards the center of the fluid core stream in the cuvette 110. In an embodiment, the third air-coupled laser source 302 can be such that it produces the third laser beam 304 with a vertical polarization with respect to mounting plate 106, i.e. the plane of polarization of the third laser beam 304 is essentially perpendicular to the major surfaces 114 and 116 of the mounting plate 106. In this embodiment, a waveplate similar to the waveplate 111 can be placed in between the third beam-shaping optic system 306 and the cuvette 110, to rotate the third laser beam 304 produced by the third air-coupled laser source 302 by a polarization angle of 90°. If the third laser beam 304 emitted by the third air-coupled laser source 302 has a horizontal polarization with respect to the mounting plate 106, i.e. the plane of polarization of the third laser beam 304 is essentially parallel to the major surfaces 114 and 116 of the mounting plate 106, the waveplate similar to the waveplate 111 can be removed.

Figure 4:
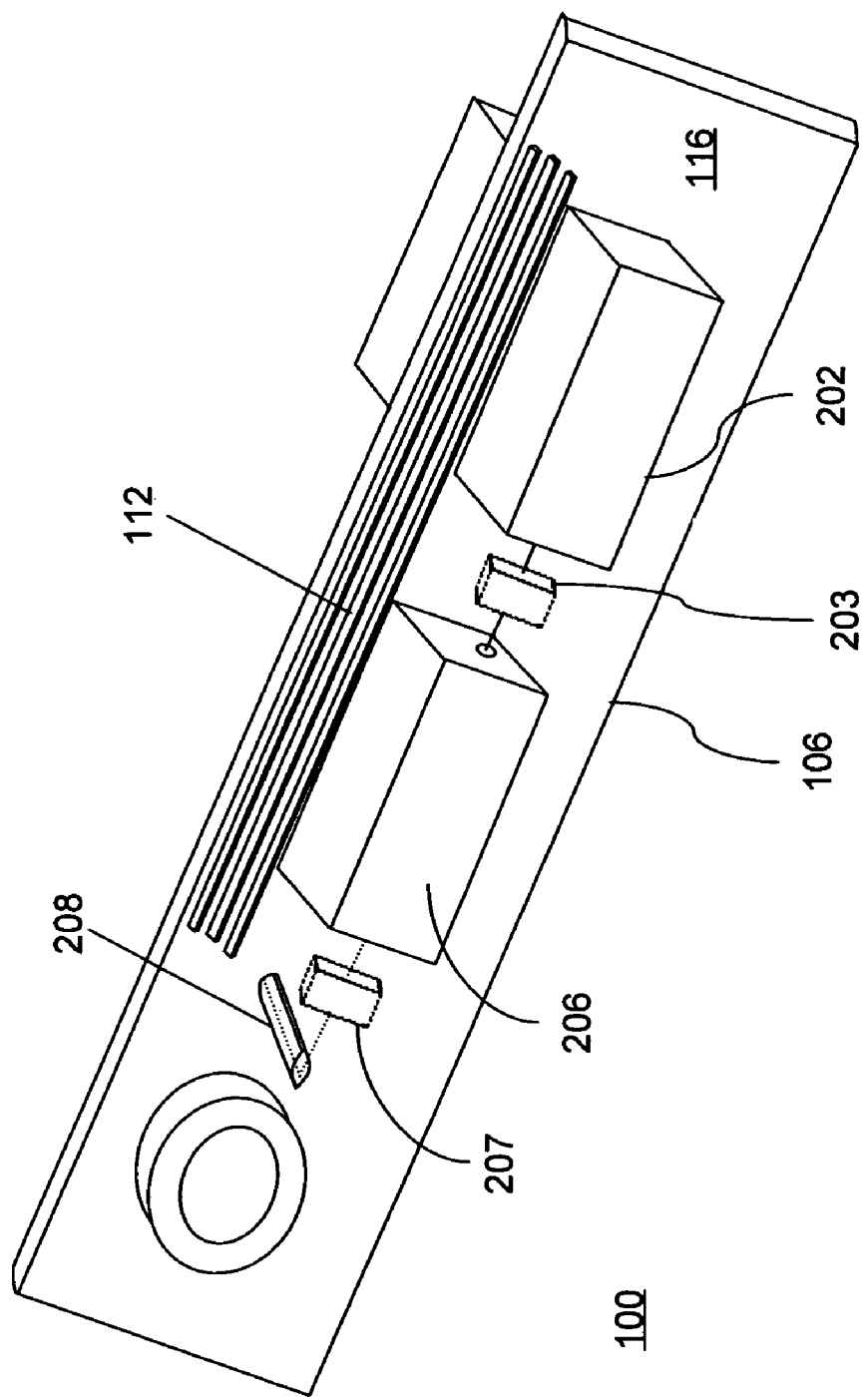
FIG. 4 illustrates a back view of the flow cytometer, in accordance with an embodiment of the present invention.

FIG. 4 illustrates a back view of the flow cytometer 100, in accordance with an embodiment of the present invention. The back view of the flow cytometer 100, as shown in FIG. 4, illustrates the position of the second air-coupled laser source 202 and the second beam-shaping optic system 206 in the architecture of the flow cytometer 100. The second air-coupled laser source 202 is mounted on the second major surface 116 of the mounting plate 106. In an embodiment, a fourth air-coupled laser source can be placed above or below the second laser source 202, on the second major surface 116 of the mounting plate 106. In the event of overheating, the plurality of fins 112 can transfer the heat to the atmosphere to cool all the air-coupled laser sources present in the flow cytometer 100.

Although the invention, described with the help of FIGS. 1 to 4, is shown to include a maximum of three air-coupled laser sources, it will be apparent to those with ordinary skill in the art that more than three air-coupled laser sources can be included, without departing from the spirit or the scope of the invention.

Various embodiments of the present invention offer one or more advantages. The present invention provides the architecture of air-coupled laser sources in a flow cytometer. The system eliminates the need for fiber-optic cables to direct laser beams to the fluid core stream, thereby reducing loss of laser energy to the environment. Further, the use of the plurality of spacers with appropriate coefficients of thermal expansion in the invention reduces the effects of thermal expansion on the alignment of the air-coupled laser sources with respect to the cuvette by equalizing thermal expansion throughout the flow cytometer, thereby reducing the possibility of erroneous results in the analysis.

What is claimed is:

1. A flow cytometer, the flow cytometer comprising:
    a mounting plate with a first major surface and a second major surface;
    a cuvette mounted on the first major surface, the cuvette adapted to provide a fluid core stream therethrough so that the fluid core stream flows essentially parallel to the first major surface of the mounting plate;
    a first air-coupled laser source mounted on the first major surface, the first air-coupled laser source generating a first laser beam essentially perpendicular to the fluid core stream; and
    a second air-coupled laser source mounted on the second major surface, the second air-coupled laser source generating a second laser beam essentially perpendicular to the fluid core stream, wherein the first laser beam and the second laser beam facilitate an analysis of the fluid core stream.

2. The flow cytometer according to claim 1 further comprising a first beam-shaping optic system corresponding to the first air-coupled laser source, the first beam-shaping optic system mounted to receive the first laser beam from the first air-coupled laser source and focus the first laser beam at a center of the fluid core stream.

3. The flow cytometer according to claim 1 further comprising a second beam-shaping optic system corresponding to the second air-coupled laser source, the second beam-shaping optic system mounted to receive the second laser beam from the second air-coupled laser source and focus the second laser beam at a center of the fluid core stream.

4. The flow cytometer according to claim 1 further comprising a plurality of spacers to maintain a predefined distance between the mounting plate and at least one of the first air-coupled laser source and the cuvette.

5. The flow cytometer according to claim 1, wherein the first laser beam has a vertical polarization with respect to the mounting plate.

6. The flow cytometer according to claim 4, wherein the first beam-shaping optic system comprises a first waveplate, and wherein the first waveplate rotates the first laser beam by a polarization angle of 90°.

7. The flow cytometer according to claim 1 further comprising at least one mounting bracket to facilitate mounting of the first air-coupled laser source on the mounting plate.

8. The flow cytometer according to claim 1, wherein the second laser beam has a vertical polarization with respect to the mounting plate.

9. The flow cytometer according to claim 1, wherein the second beam-shaping optic system comprises a second waveplate, and wherein the second waveplate rotates the second laser beam by a polarization angle of 90°.

10. The flow cytometer according to claim 1 further comprising at least one mounting bracket to facilitate mounting of the second air-coupled laser source on the mounting plate.

* * * * *